United States Patent [19]
Sutcliffe

[11] Patent Number: 5,470,310
[45] Date of Patent: Nov. 28, 1995

[54] MODULAR NIGHT SPLINT

[76] Inventor: Brian L. Sutcliffe, c/o James E. Ogden, Block Box 7-47, Ephraim, Utah 84627

[21] Appl. No.: 196,479

[22] Filed: Feb. 15, 1994

Related U.S. Application Data

[62] Division of Ser. No. 913,294, Jul. 14, 1992, Pat. No. 5,382,225.

[51] Int. Cl.$^6$ ..................................................... A61F 5/00
[52] U.S. Cl. ............................................. 602/24; 128/882
[58] Field of Search ...................... 602/24, 25, 27–29, 602/8, 23; 128/882

[56] References Cited

U.S. PATENT DOCUMENTS

| | | | |
|---|---|---|---|
| 3,777,747 | 12/1973 | Friedman | 602/24 |
| 3,892,231 | 7/1975 | Tummillo | 602/24 |
| 3,931,817 | 1/1976 | Infranca | 602/24 |
| 4,040,416 | 8/1977 | Zentman | 602/24 |
| 4,088,129 | 5/1978 | DiGiulio | 602/24 |
| 4,249,523 | 2/1981 | Bidwell | 602/24 |
| 4,336,795 | 6/1982 | Nichols | 602/24 |
| 4,412,536 | 11/1983 | Kurtz et al. | 602/24 |
| 4,520,803 | 6/1985 | Quest | 602/24 |
| 4,550,772 | 11/1985 | Kurtz et al. | 602/24 |
| 4,570,620 | 2/1986 | Kurtz et al. | 602/24 |

FOREIGN PATENT DOCUMENTS

| | | | |
|---|---|---|---|
| 550842 | 7/1993 | European Pat. Off. | 602/25 |

Primary Examiner—Linda C. M. Dvorak

[57] ABSTRACT

A plurality of modular night splints for treatment of different infant foot deformities. The splints comprise a pair of top plates (36 and 37) with base plates (33)1 or foot plates (30) having rotating wedges (49) adjustment mechanisms to which can be added a back leg assembly (44), with a dynamic modular dorsiflexory splint which is able to correct in multiple planes of adjustment simultaneously. In compound deformity problems the modular splint allows the following simultaneous functions:

1. abduction/adduction of the foot to the 2. abduction/adduction of the forefoot to the rearfoot, 3. varus/valgus relationship of the rearfoot to the 4. varus/valgus relationship of the forefoot to the rearfoot, 5. dorsiflexion/plantarflexion of the foot and leg, and 6. abduction/adduction of foot and leg to cardinal sagittal plane. The multiple correction capabilities of the splint are made possible by mounting adjustable top plates (36 and 37) onto adjustable base plates (33), which are in turn mounted either to a spreader bar (23), or to a back leg assembly (44), or to both. This physical configuration makes it possible to articulate the feet in multiple planes with a very simple, easy-to-use and adjust modular splint.

13 Claims, 7 Drawing Sheets

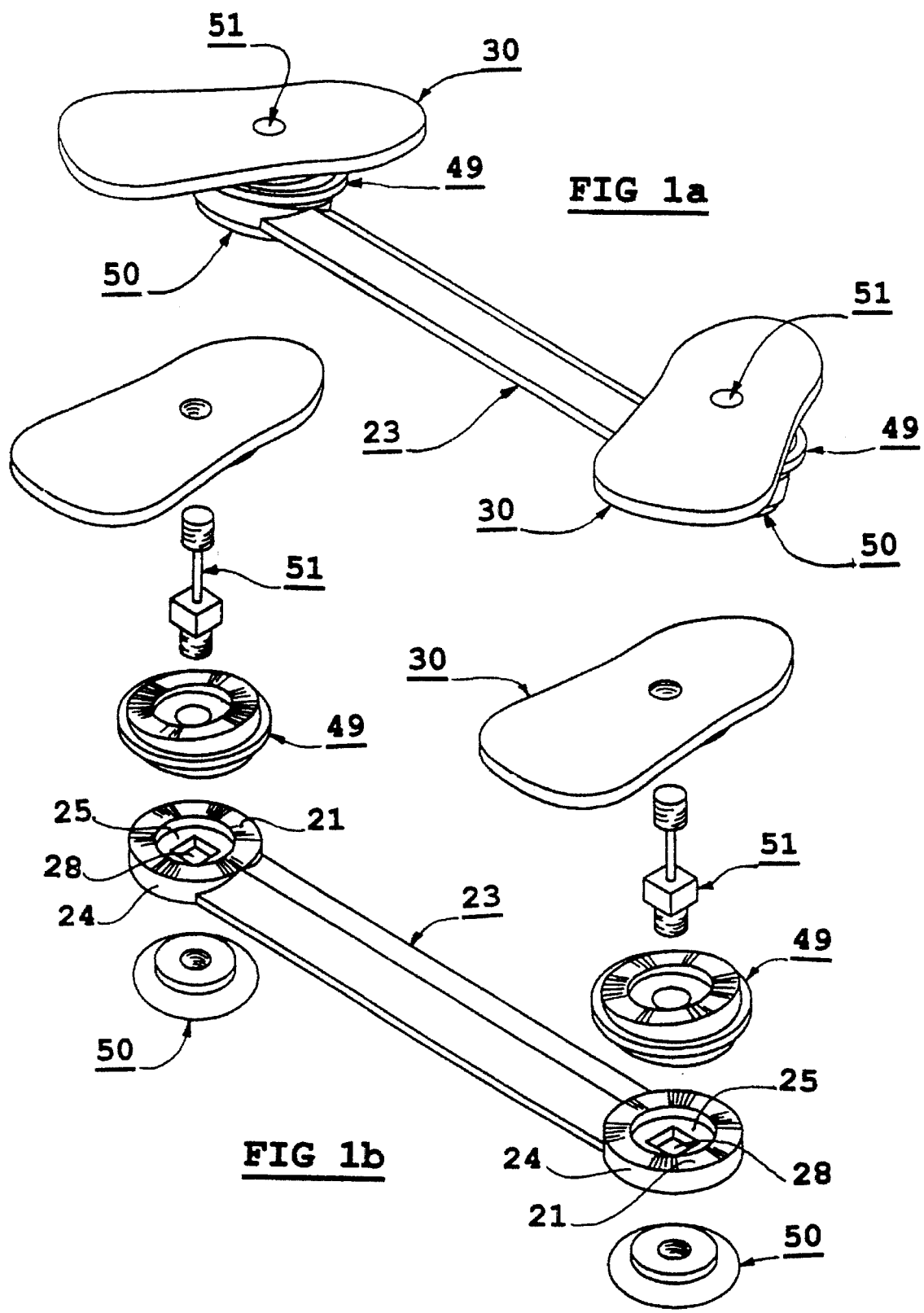

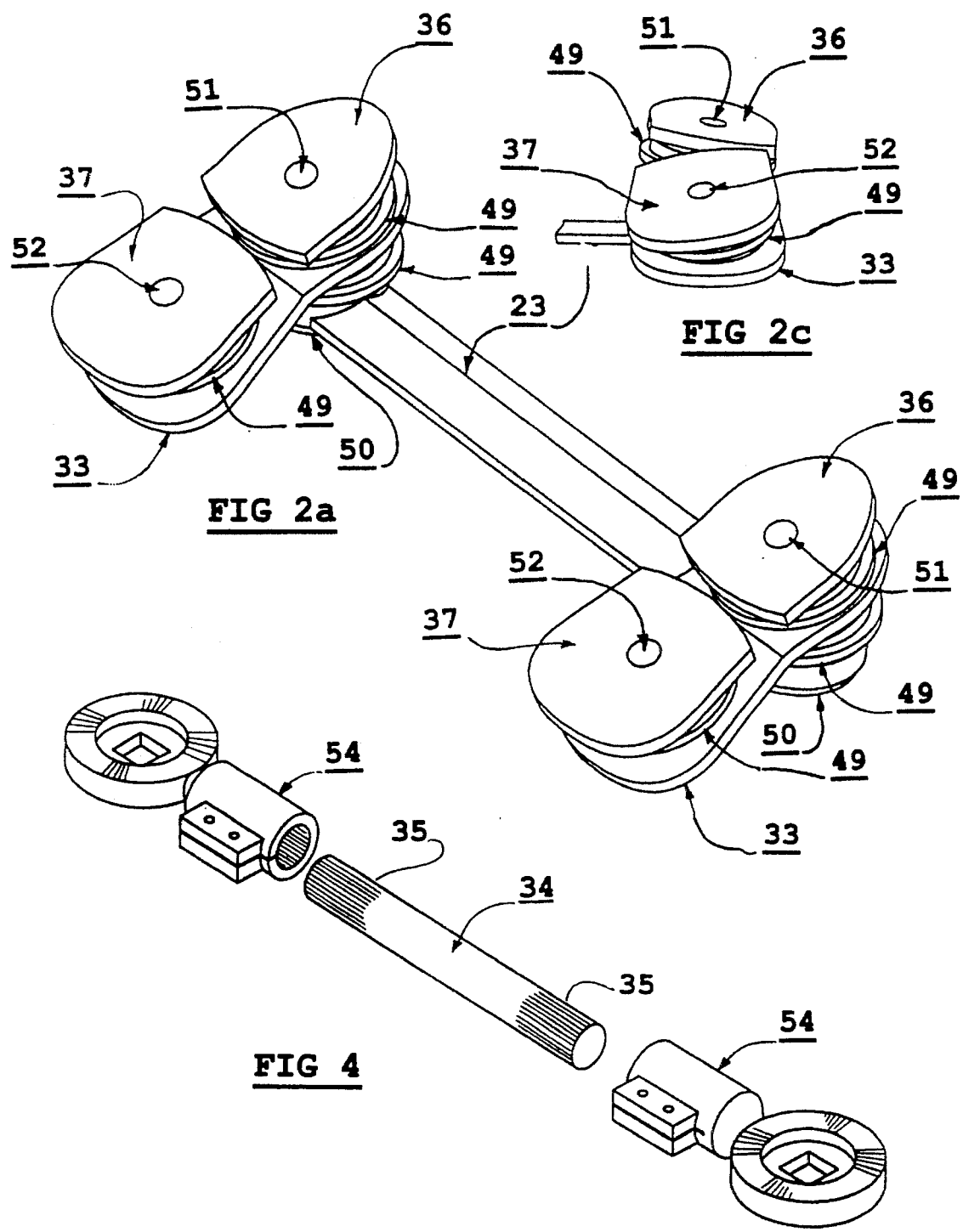

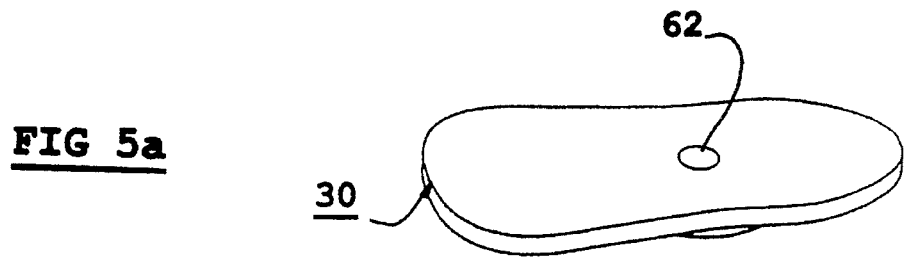
FIG 5a
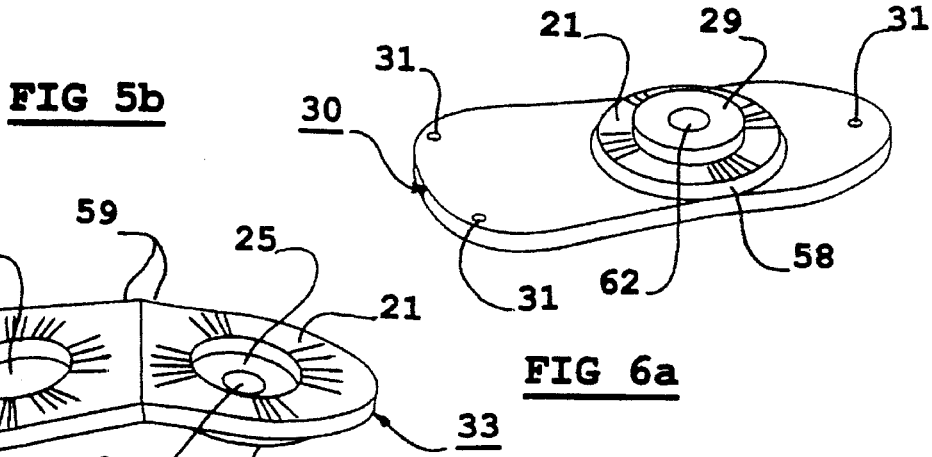
FIG 5b
FIG 6a
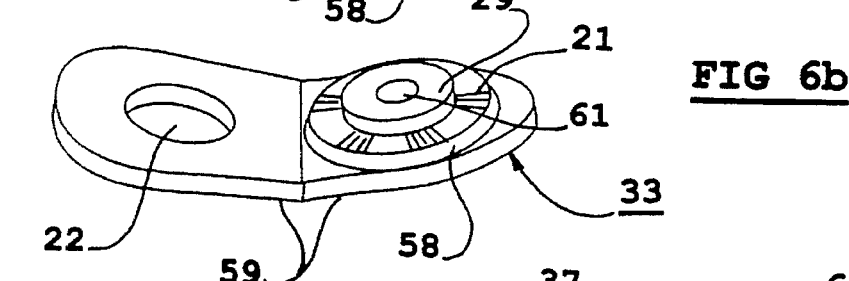
FIG 6b
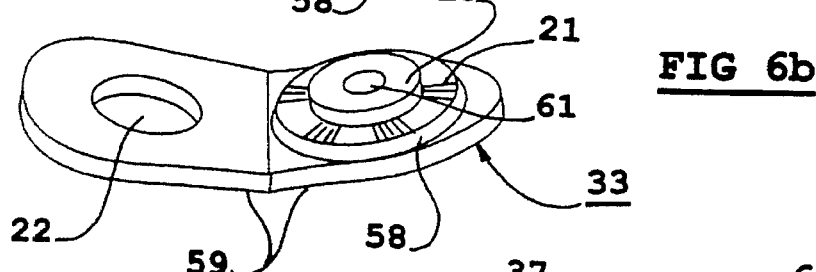
FIG 7a
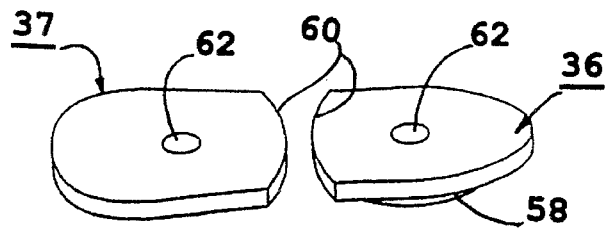
FIG 7b
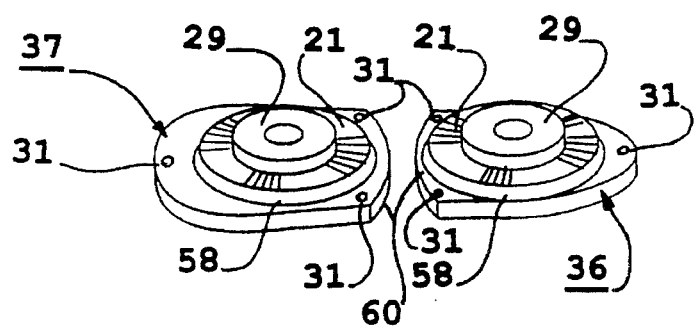

MODULAR NIGHT SPLINT

This is a division of Ser. No. 07/913,294 filed Jul. 14, 1992 now U.S. Pat. No. 5,382,225.

BACKGROUND—FIELD OF THE INVENTION

This invention relates to an orthopedic foot splint, particularly to one which is useful in correcting bone and positional deformities by holding a patient's feet, and/or legs, in appropriate corrective positions.

BACKGROUND—DISCUSSION OF PRIOR ART

Some children are born with genetic deformities to their feet and some have iatrogenic (caused by doctors influence) deformities and some with deformities caused by growing in an improper position in the womb.

The medical profession treats these deformities with various means which move the bones of the foot into their correct positions. Some physicians choose to withhold treatment, because in a certain percentage of cases the patient will grow out of the problem.

For those physicians who choose to treat the problem, the following methods of treatment are available:

1. casting,
2. surgery, usually followed by casting or splints,
3. orthotic devices or inserts for shoes,
4. orthotic shoes, and
5. braces or splints.

Braces or splints can be used because the bones of the lower extremities in infants and young children are not fully formed and are malleable to a certain extent. Therefore, by encouraging a malformed foot into a new and correct position and holding it there until the foot has adapted to the new and correct position, the malformation of the foot can usually be ameliorated. Splints are in common use to perform this corrective function.

However, currently available splints have been limited in their ability to address the correction of multiple-deformity problems. Therefore, although most splints may be used to treat one deformity, they cannot treat other deformities at the same time. Thus, the other deformities may become fixed and untreatable with splints and require a more invasive and costly treatment, such as surgery.

Although a few prior-art devices have been conceived that could address the problem of multiple deformities, they have not been accepted in the marketplace for various reasons:

1. they are awkward to use,
2. the design is impractical for the use intended,
3. they are difficult to adjust or keep in adjustment,
4. the expense of manufacture is too great, or
5. for reasons of appearance, cost to the patient, or difficulty in application.

This gave rise to the need for a device that could adjust or correct in several planes of adjustment simultaneously that was simple, attractive, cost efficient, easy to install, use, and adjust, etc.

Thus, splints with a rotating wedge were conceived to resolve these problems.

One common type of prior-art splint of this type is disclosed in U.S. Pat. Nos. 3,910,267, 1974, and 3,973,559, 1975, to Reiman. However, this splint merely hold a patient's feet in a fixed position and has no adjustment capability.

Another splint of this type is shown in U.S. Pat. No. 4,040,416, 1977, to Zentman. Zentman's splint, however, corrects abduction/adduction (toe in/toe out) of the foot to the leg only. (Abduction/adduction is the motion occurring on the transverse plane during which the distal aspect of the foot moves away from (abduction), or towards (adduction) the midline of the body about a vertical axis of rotation located at the proximal aspect of the foot).

U.S. Pat. No. 3,892,231, 1975, to Tummillo does allow for a limited amount of abduction/adduction adjustment between the forefoot and rearfoot ("C" shaped foot or severe flat foot) as well as abduction/adduction of the foot to the leg. The patient's subtalar joint must first be stabilized before the foot is rotated in order to prevent the possibility of causing flat feet. However, this splint does not perform this function. (The subtalar joint is formed by the appositional articular surfaces of the talus and calcaneous).

Although there are splints, of the type disclosed in U.S. Pat. No. 4,263,901, 1981, to Nichols, that do tilt to stabilize the subtalar joint. These splints tilt and rotate only and are not capable of any other corrective adjustment.

Other common types of prior-art splints, are disclosed in U.S. Pat. Nos. 4,249,523, 1981, to Bidwell, and 4,413,536, 1983, 4,481,940, 1984, and 4,495,943, 1985, to Kurtz. While allowing more mobility to the patient, thereby effectively alleviating the subtalar joint problem, these still correct only abduction/ adduction of the foot to the leg. When the patient places one foot close to the other, or crosses the feet even slightly while attempting to walk, parallelogram components in the splint interfere with each other, presenting a trip hazard.

U.S. Pat. No. 3,777,747, 1973, to Friedman shows a splint which requires a specially made shoe to effectively mount to the splint and does not address abduction/adduction of the forefoot to the rearfoot. Friedman's splint is complex and difficult to adjust, especially as a change in one adjustment may require a compensating change to other adjustments.

U.S. Pat. No. 4,570,620, 1986, to Kurtz merely shows a baseplate for a shoe, which is designed for use in conjunction with a splint. By itself this device is capable of torsional adjustment in an oblique plane only and nothing else.

None of the beforementioned splints are modular in nature, allowing features to be added or taken away as needed for the treatment of the patient. Also, none of the beforementioned splints correct dorsiflexion/plantarflexion problems or are capable of simultaneous correction in all splint correctable planes. (Dorsiflexion/plantarflexion is the motion occurring on the cardinal sagittal plane during which the distal aspect of the foot moves toward [dorsiflexion], or away from [plantarflexion] the tibia about an axis of rotation located at the proximal aspect of the foot. The cardinal sagittal plane is a flat imaginary vertical plane passing through the body from front to back, dividing it into a right half and a left half. Varus/valgus is a fixed structural position which the foot would assume if it were inverted [varus] or everted [valgus]).

OBJECTS AND ADVANTAGES

Accordingly, several objects and advantages of the present invention are to provide an adjustable modular splint which is capable of tilting the foot to stabilize the subtalar joint, and which could allow the patient to be ambulatory.

Other objects and advantages are to provide a modular splint with additional simultaneous functions, including abduction/adduction of the forefoot to the rearfoot, varus/ valgus (heel tilting in/out) relationship of the rearfoot to the leg, varus/valgus relationship of the forefoot to the rearfoot (forefoot tilting in/out, heel tilting in/out), dorsiflexion/ plantarflexion of the foot and leg, and abduction/adduction of foot and leg to the cardinal sagittal plane.

Simultaneous adjustment of common splint-treatable infant foot deformities may reduce the treatment time required, thereby reducing or even eliminating the need for future surgery.

Another object is to provide a modular splint for use at night. A modular night splint may be easily adjusted to accommodate each patient's required positional correction parameters without disassembly. The modular night splint may be adjusted, either on or off the patient, with precise and prescribable settings.

The modular night splint has the ability to restore the correct position of, and support the arch of the foot. When the foot is operated on to alter its structure, the modular night splint may be utilized to hold or position the foot for x-ray position verification prior to placing a cast on the foot and leg. Casting may be used in conjunction with the modular night splint.

Further features, objects and advantages of the present invention are stated in or will be apparent from the detailed description and drawings of the presently preferred embodiments of the invention.

BRIEF DESCRIPTION OF DRAWING FIGURES

FIG. 1a is a perspective view of a wedge operated bi-plane embodiment of an assembled modular night splint in accordance with the invention.

FIG. 1b is an exploded view of the splint of FIG. 1a.

FIG. 2a is a perspective view of a wedge operated quadra-plane embodiment of an assembled modular night splint in accordance with the invention.

FIG. 2b is an exploded view of the splint of FIG. 2a.

FIG. 2c is a frontal view of the splint of FIG. 2a showing forefoot to rearfoot adjustment.

FIG. 4 is a perspective view of an alternative bar and female adaptors alternatively used in FIGS. 1a through 3 embodiments.

FIG. 5a is a perspective view showing the upper-surface of a foot plate as shown in FIGS. 1a and 1b.

FIG. 5b is a perspective view of the under-surface of a foot plate as shown in FIGS. 1a and 1b.

FIG. 6a is a perspective view of the upper-surface of a base plate as shown in FIGS. 2a through 3.

FIG. 6b is a perspective view of the under-surface of a base plate as shown in FIGS. 2a through 3.

FIG. 7a is a perspective view of the upper-surface of the top plates as shown in FIGS. 2a through 3.

FIG. 7b is a perspective view of the under-surface of the top plates as shown in FIGS. 2a through 3.

LIST OF REFERENCE NUMERALS

Figure 2B:
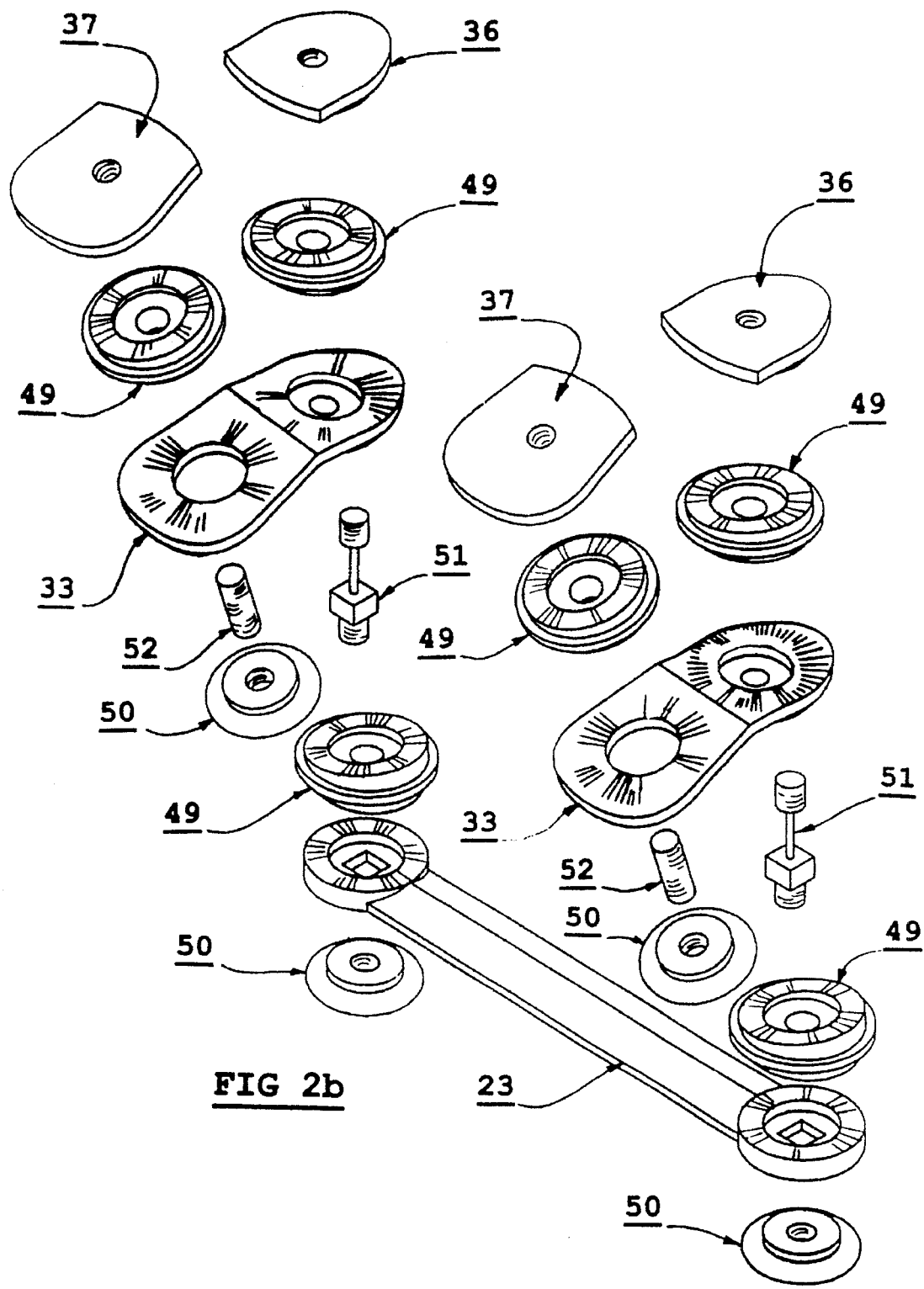

| | | | |
|---|---|---|---|
| 21 | serrated clutch face | 49 | rotating wedge |
| 22 | large hole | 50 | nut |
| 23 | spreader bar with chevron cross section | 51 | flexible bolt |
| | | 53 | male splined adaptor |
| 24 | annular ring | 54 | female splined adaptor |
| 25 | circular depression | 55 | female round extension |
| 26 | cylinder | 56 | male round extension |
| 27 | protruding annulus | 57 | dihedral acclivity (two faced, sloped) |
| 28 | square hole | | |
| 29 | raised alignment cylinder | 58 | raised circular base |
| 30 | foot plate | 59 | inverted synclined surface (inverted V) |
| 31 | depressions | | |
| 42 | retaining strap | 60 | arc |
| 43 | calf body | 61 | small round hole |
| 44 | back leg assembly | 63 | vertical bar |
| 45 | threaded portion | 64 | calf cup |
| 46 | counter rotational shoulder | 65 | protruding annular ring |
| | | 66 | shallow annular groove |
| 47 | flexible narrow neck | 71 | rectangular bar |

DESCRIPTION OF MODULAR NIGHT SPLINT

The presently preferred embodiments of the modular night splint are depicted in FIGS. 1 through 13, and include shoes (not shown) which the patient wears when using the splint.

The splint has right and left hand sides which are both assembled in like manner, therefore assembly of only one side is described. The patient's shoe (not shown) may be affixed to the splint by screws, rivets, glue, or any other appropriate means, well-known in the art.

The names of the various embodiments of the modular night splint refer to the number of planes or types of adjustment which that particular embodiment is capable of, or commonly used for, correcting.

Splints of this type are usually worn at night when the patient is sleeping because of restriction to the patient's mobility (hence the term "night splint").

Structure-Wedge Operated Bi-Plane Embodiment

FIGS. 1 and 1a show a splint for treatment of abduction/ adduction of the foot to the leg, comprising foot plates 30, flexible bolts 51, rotating wedges 49, a spreader bar 23 and nuts 50.

Detail—Wedge Operated Bi-Plane Embodiment

The top view of the plate 30, as shown in FIG. 5a, is an approximation of the outline of a shoe. The plate 30 comprises a planar upper-surface for receiving the shoe of the patient. The under-surface of the plate 30 has depressions 31 for locating fasteners (not shown) used to affix the plate 30 to the shoe of the patient. The plate 30 has a raised circular base 58 with a serrated clutch face 21, a raised alignment cylinder 29 with a threaded hole 62 extending through its center. The plate 30 can also receive a custom made orthotic (not shown, well known in the art) which is capable of mounting the patient's foot directly without a shoe.

Figure 9:
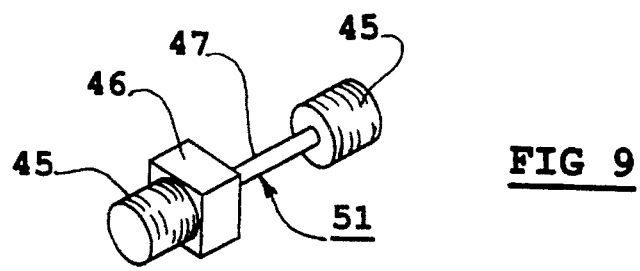
FIG. 9 is a perspective view of a flexible bolt as shown in FIGS. 1a through 2b.

The bolt 51, as shown in FIG. 9, comprises a threaded portion 45 on each end, separated by a flexible narrow neck 47, and a counter rotational shoulder 46. The shoulder 46 prevents torsional damage to the neck 47.

Figures 8A, 8B, 8C:
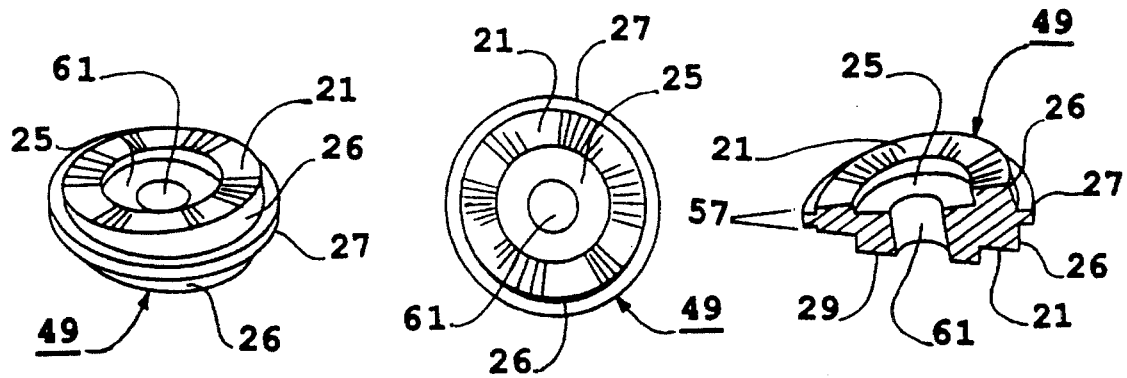
FIG. 8a is a perspective view of a rotating wedge used in FIGS. 1a through 3 embodiments.
FIG. 8b is a top view of a rotating wedge used in FIGS. 1a through 3 embodiments.
FIG. 8c is a sectional view of a rotating wedge used in FIGS. 1a through 3 embodiments.

The wedge 49, as shown in FIGS. 8a, 8b, and 8c comprises a cylinder 26 with a protruding annulus 27 about its midsection and a dihedral acclivity 57 on the top and bottom surface. The wedge 49 has a clutch 21 on each surface, the upper-surface has a circular depression 25. The bottom surface of the wedge 49 has a cylinder 29 with a round hole 61 extending through the center. The hole 61 joins the axes of the cylinder 29 and depression 25.

Figure 3:
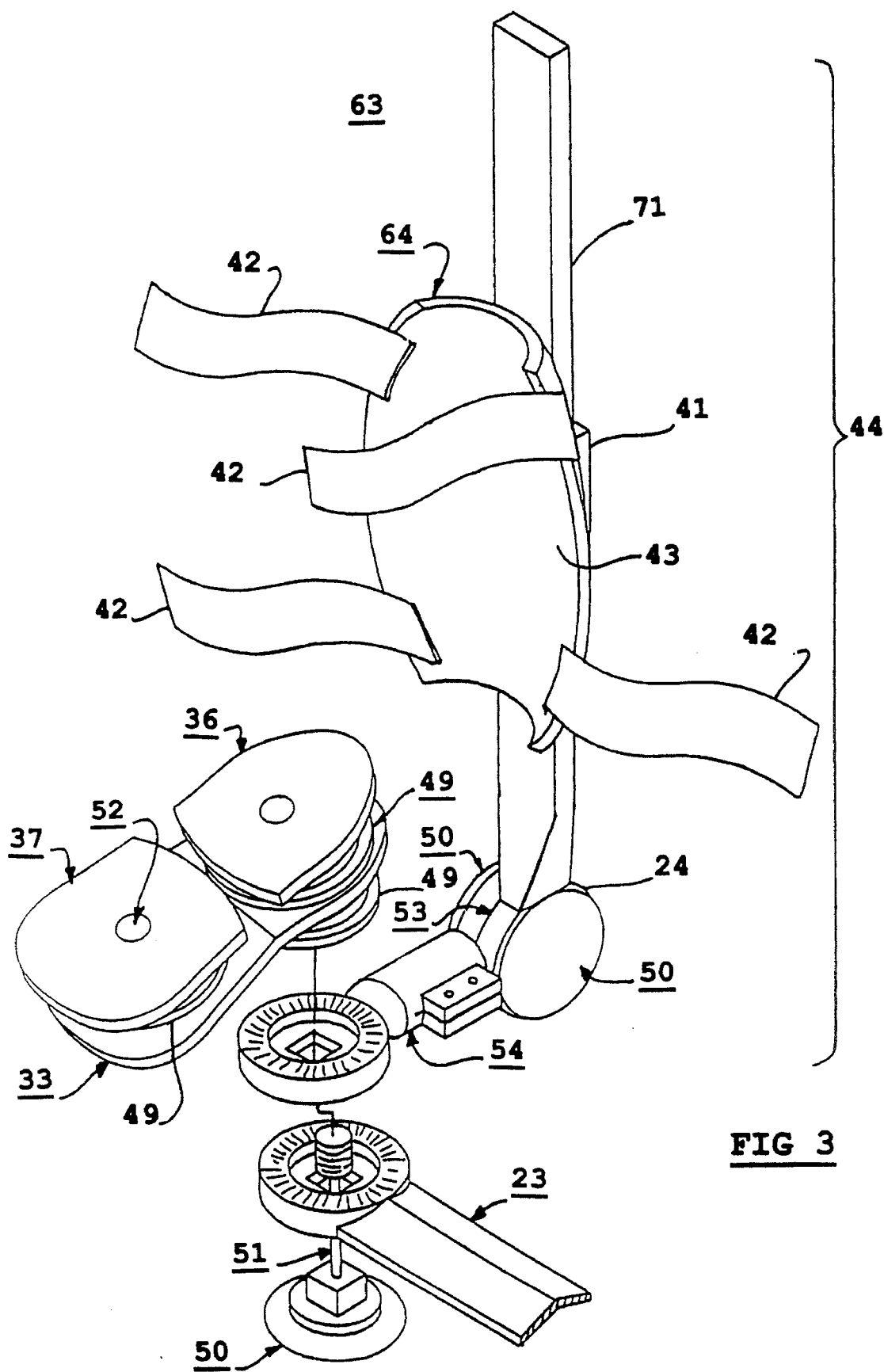
FIG. 3 is a perspective view of a hexa-plane embodiment of a modular night splint in accordance with the invention.

The bar 23, as shown in FIGS. 1 through 3, comprises an annular ring 24 at each end of a chevron cross sectioned middle portion. The upper-surface of the ring 24 has a clutch 21, and a depression 25. The Under-surface of the ring 24 has depression 25. A square hole 28 extends through the center of the ring 24. The length of the bar 23 usually approximates the shoulder width of the patient (at the discression of the treating physician).

The nut 50, as shown in FIGS. 1a through 3 and 11, comprises a nut body 40 with a cylinder 29 and a blind hole 62 in the upper-surface. The body 40 of the nut 50 can also be a walking nut made from a non-slip rubber or plastic material (as commonly used in the art), in a size approximately the width of the patient's foot, and in a configuration suitable for walking on (not shown, commonly used in the art).

Assembly—Wedge Operated Bi-Plane Embodiment

Figures 10A, 10B:
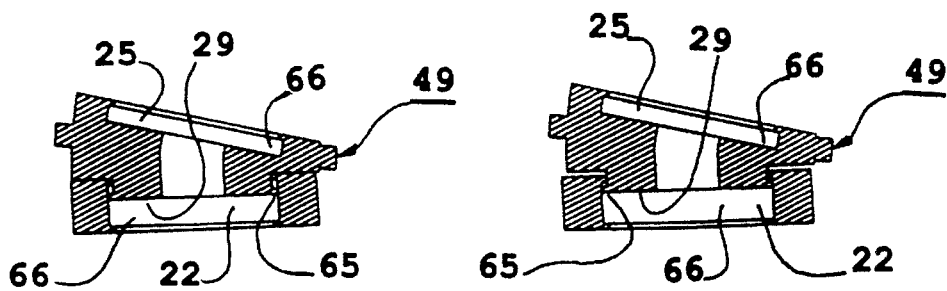
FIG. 10a is a sectional view of a rotating wedge and annular ring shown in FIGS. 1a through 3 illustrating the snap-together feature in the fully closed position (locked).
FIG. 10b is a sectional view of a rotating wedge and annular ring shown in FIGS. 1a through 3 illustrating the snap-together feature in the open position (freely rotating).
Figure 11A:
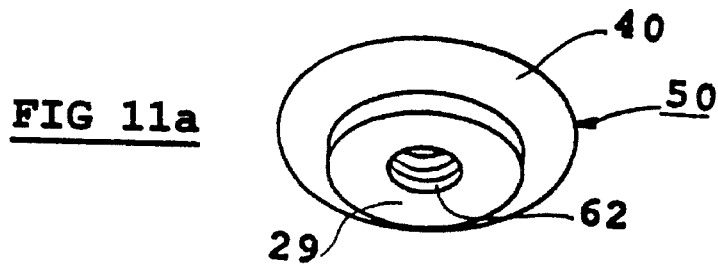
FIG. 11 is a perspective view of a nut used for wedge operated splints as shown in FIGS. 1a through 3 embodiments.
Figure 11B:
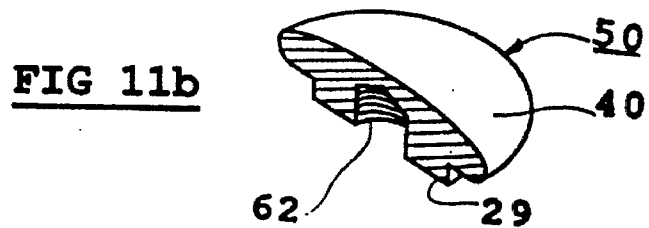
Figure 12:
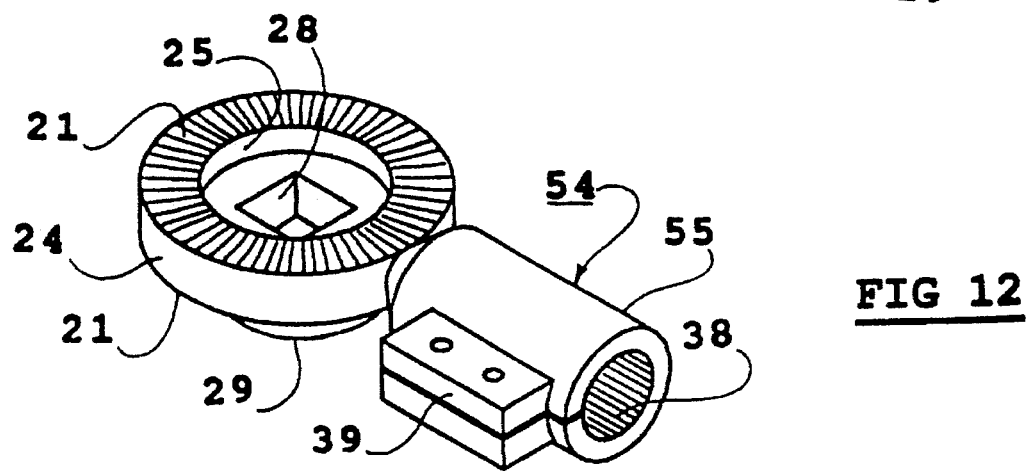
FIG. 12 is a perspective view of a female adaptor used in FIG. 4 embodiment.

To assemble the splint, the patient's shoe is affixed to a plate 30, which is inserted into a wedge 49, which is in turn inserted into the bar 23. The assembly is held in place by the snap-together protruding annular rings 65 and shallow annular grooves 66, as shown in FIGS. 10a and 10b. The assembly is secured by the nut 50 and bolt 51.

Operation—Wedge Operated Bi-Plane Embodiment

For treatment of abduction/adduction of the foot to the leg, the nut 50 is loosened and the wedge 49 is rotated about its vertical axis. Rotation of the wedge 49 tilts the plate 30 and shoe, thereby achieving the angle necessary to stabilize the patient's subtalar joint. Then the patient's shoe, plate 30, and wedge 49 may be rotated, together as a unit, about the pivot axis of wedge 49. This sub-assembly is then rotated to the desired toe-in/toe-out position, and fixed in position by re-tightening the nut 50. Tightening the nut 50 applies tension between the plate 30 and nut 50 by means of the bolt 51, thus positively engaging the clutch 21.

The adjusted position is usually a small movement opposite the direction of malformation. This movement is gradually and incrementally increased over a period of time until a maximum adjustment is reached. The splint is used until correction of the malformation is attained or until the physician determines that cessation of treatment or another mode of treatment is in order.

Structure—Wedge Operated Quadra-Plane Embodiment

FIGS. 2a through 2c show a splint for treatment of abduction/adduction of the foot to the leg, abduction/adduction of the forefoot to the rearfoot, varus/valgus relationship of the rearfoot to the leg, and varus/valgus relationship of the forefoot to the rearfoot. The splint comprises top plates 36 and 37, wedges 49, base plates 33, bolts 51, rigid bolts 52, a bar 23, and nuts 50.

Detail—Wedge Operated Quadra-Plane Embodiment

The top view of plates 36 and 37, as shown in FIGS. 7a and 7b, is similar to the plate 30, only divided into two portions by arcs 60. Plates 36 and 37 comprises a planar upper-surface for receiving the shoe of the patient. The under-surface of plates 36 and 37 has depressions 31 for locating the fasteners (not shown) used to affix to the shoe of the patient. Plates 36 and 37 each have a base 58, a clutch 21, a cylinder 29, and a hole 62 extending through the center. Plates 36 and 37 can also receive a custom made orthotic (not shown, well known in the art) which is capable of mounting the patient's foot directly without the need for a shoe.

Plate 33, as shown in FIGS. 6a and 6b, comprises an inverted synclined upper-surface 59, with a large hole 22 in the toe portion and a depression 25 in the heel portion. The clutch 21 surrounds the hole 22, and depression 25, with a hole 61 extending through the heel portion. The under-surface of the plate 33 heel portion has a base 58 with a clutch 21 and a cylinder 29.

Assembly—Wedge Operated Quadra-Plane Embodiment

The patient's shoe sole is split into a heel and toe portion, then affixed to plates 36 and 37 which are inserted into wedges 49. Wedges 49 are then inserted into the plate 33, which is in turn inserted into another wedge 49. The assembly is then inserted into the bar 23. The assembly is held in place by the snap-together rings 65 and grooves 66 and is secured by nuts 50 and bolts 51, and 52.

Operation—Wedge Operated Quadra-Plane Embodiment

Treatment of abduction/adduction of the foot to the leg, and varus/valgus relationship of the rearfoot to the leg, is accomplished in a similar manner as with the adjustment of the wedge operated bi-plane splint embodiment. For treatment of abduction/adduction of the forefoot to the rearfoot, nuts 50 are loosened and plates 36 and 37 are rotated about their vertical axes to an appropriate corrective position. For treatment of varus/valgus relationship of the forefoot to the rearfoot, as shown in FIG. 2c, wedges 49 under plates 36 and 37 are rotated to achieve an appropriate adjustment. Re-tightening nuts 50 applies tension between plates 36 and 37 and nuts 50 by means of bolts 51 and 52, thereby positively engaging clutches 21.

Structure—Wedge Operated Hexa-Plane Embodiment

FIG. 3 shows a splint for treatment of abduction/adduction of the foot to the leg, abduction/adduction of the forefoot to the rearfoot, varus/valgus relationship of the rearfoot to the leg, varus/valgus relationship of the forefoot to the rearfoot, and for dorsiflexion/plantarflexion and equinus/equino problems. To the wedge operated quadra-plane splint embodiment, a back leg assembly 44 is added. The back leg assembly 44 comprises a calf cup 64, a vertical bar 63, a bolt 52 (not shown in FIG. 3, bolt 52 is located between nuts 50), nuts 50, a female splined adaptor 54, and a male splined adaptor 53. (Equinus/equino problems are associated with a shortage of the calf muscle and tendons.)

Detail—Wedge Operated Hexa-Plane Embodiment

The cup 64 comprises a calf body 43 which approximates the contours of the back of the lower leg of the patient and is padded (padding not shown) to accommodate variations in the patient's conformation (body shape or contours), and which has a slide guide 41 and retaining straps 42.

The bar 63 comprises a rectangular bar 71, with a ring 24 on its end. The ring 24 has a clutch 21 on one surface and a hole 22 extending through its center.

The female adaptor 54, as shown in FIG. 12a, comprises a ring 24 with a clutch 21 on each surface, one surface has a cylinder 29 and the other has a depression 25. A hole 28 extends through the center of the ring 24, joining the axes of the cylinder 29 and depression 25. A round extension 55 with a female spline 38 protrudes from the side of the ring 24. The extension 55 has a clamp 39 protruding from its side for firmly locking the female spline 38 onto the male spline 35 of adaptor 53.

Figure 13:
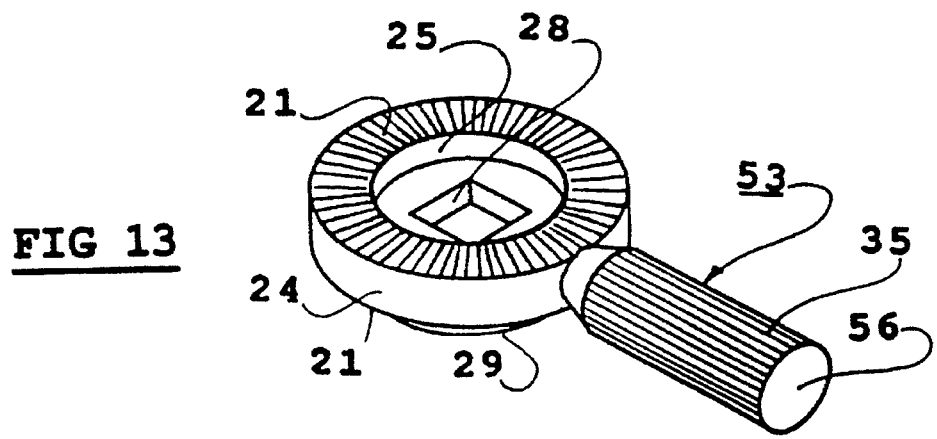
FIG. 13 is a perspective view of a male adaptor as used in a FIG. 4 embodiment.

The male adaptor 53, as shown in FIG. 13, comprises a ring 24 with a clutch 21 on one surface surrounding cylinder 29. One surface of the adaptor 53 has a cylinder 29, the other has a depression 25. A hole 28 extends through the center of the ring 24, joining the axes of the cylinder 29 and depression 25. A splined 35 round extension 56 protrudes from the side of the ring 24.

Assembly—Wedge Operated Hexa-Plane Embodiment

The bar 63 is inserted into the guide 41 of cup 64. Then this assembly is affixed to the adaptor 53 using a bolt 52 and nuts 50. Adaptor 53 is inserted into adaptor 54, and held in place with the clamp 39. The ring 24 end of adaptor 54 is then inserted between the wedge 49 and bar 23 of the wedge operated quadra-plane splint embodiment.

Operation—Wedge Operated Hexa-Plane Embodiment

Abduction/adduction and varus/valgus problems are corrected as previously described for the wedge operated quadra-plane embodiment of the splint. For dorsiflexion/plantarflexion and equinus/equino deformity problems, the angular relationship between the bar 63 and adaptor 53 is adjusted by loosening nuts 50, repositioning the back leg assembly 44 and then re-tightening nuts 50. By removing the bar 23 and using the walking nut described previously, the patient may be ambulatory. Without the bar 23, the varus/valgus relationship of the foot to the leg can be adjusted by varying the insertion angle of adaptor 53 into adaptor 54.

Structure—Alternative Bar Embodiment

FIG. 4 shows a round bar 34 with adaptors 54, an alternative embodiment of the bar 23, which comprises a bar 34 with an adaptor 54 placed on each end.

Detail—Alternative Bar Embodiment

The round bar 34 comprises a round bar with splined ends 35.

Assembly—Alternative Bar Embodiment

The splined ends 35 of bar 34 are inserted into the female spline 38 of adaptors 54. The bar 34 may be inserted into the adaptors 54 at any rotational position.

Operation—Alternative Bar Embodiment

The bar 34 and adaptors 54 may be substituted for the bar 23 in any of the presently preferred wedge operated embodiments.

Snap-Together Feature for Wedge Operated Splint Embodiments

FIG. 10a and 10b shows the presently preferred embodiment of the groove 66 and ring 65 which allows the splint components to be snapped together during assembly. This is accomplished by means of a slightly protruding annular ring 65 about the end of the cylinders 29, and a shallow annular grooves 66 in the side wall of the depressions 25 and holes 22. The depressions 25 or holes 22 and the cylinders 29 snap together in such a manner that the these splint components will freely rotate, one within the another. They can rotate freely until such time as the clutches 21 on appositional components are locked in position by the action of the nut 50 or 50a and bolt 51 or 52.

SUMMARY, RAMIFICATIONS AND SCOPE

The reader will see that I have described a modular orthopedic foot splint with the capability of multiple simultaneous corrections. The facility of multiple simultaneous correction is made possible, in part, by placing top plates (36 and 37) on moveable base plates 33. The ease of multiple simultaneous correction is made possible, in part, by rotating the rotating wedge 49, and the flexible bolt 51. The wedge 49 and bolt 51 allow a relatively simple modular device to achieve a very broad range of adjustments without complicated setup or complex instructions.

Rotation correction alone stresses the patient's subtalar joint, thereby possibly causing flat feet. The simplest embodiment of this splint will rotate and tilt in any direction approximately normal to the axis of rotation. Tilting stabilizes the patient's subtalar joint thus preserving the arch of the foot and preventing a possible causative deformity. The other embodiments will simultaneously treat increasingly complex and difficult deformities, thus effectively reducing the necessity of sequential treatment in many cases and the problems associated with the delays.

The modular night splint is a small, lightweight, easily installed and adjusted, attractively designed medical device that will perform multiple simultaneous correction of, and adjustment to, infant or child foot deformities.

The modular night splint is applied to foot deformities, such as calcaneal varus, calcaneal valgus, vertical talus, metatarsus adductus, metatarsus adductal varus, metatarsus adductal valgus, talipes equinas, talipes equino valgus, talipes equino varus, and talipes equino adducto varus.

The modular night splint has the capability of making each foot and leg completely independent of the other for walking purposes.

Although the description above contains many specificities with respect to exemplary embodiments thereof, these should not be construed as limiting the scope of the invention but as merely providing illustrations of the presently preferred embodiments. It will be understood by those of ordinary skill in the art that variations and modifications may be affected within the scope and spirit of the invention. For example, bar 23 can have other cross-sectional shapes, clutch 21 can have other interlocking interfacings to affix position, etc. The specific materials and dimensions indicated can be changed to other suitable materials and dimensions. Thus the scope of the invention should be determined by the appended claims and their legal equivalents, rather than by the examples given.

What is claimed is:

1. In a modular orthopedic foot splint to which the shoes or feet of a patient are attached, and which comprises:
   a. a pair of foot plates to which the shoes or feet of the patient can be attached, and
   b. an elongated bar interconnecting the foot plates, an improvement comprising:
   c. means for enabling said foot plates to rotate and tilt with respect to said bars, and
   d. a pair of rotating wedges for rotating and tilting said foot plates in relation to said bar,
   said pair of rotating wedges positioned in a generally stacked planar relationship with said pair of foot plates, wherein tilting and rotating of said foot plates can be accomplished by rotation of said wedge components, so that the patient's feet can be tilted to protect the patient's subtalar joint, and rotated to correct positional deformities.

2. An orthopedic foot splint as in claim 1, further comprising a plurality of flexible bolts, which allow misalignment of the ends of each bolt from the longitudinal axis thereof, said bolts for holding said foot plates, said rotating wedges, and said bar, in fixed positions relative to each other.

3. The orthopedic foot splint of claim 2 wherein said bolts also comprise a counter-rotational component for preventing rotational torque from being transmitted to a flexible portion thereof, whereby said components can be held in tight proximity one to another and locked in position by said bolts.

4. An orthopedic foot splint as in claim 1, further including means for enabling said foot plates, said wedges, and said bar to snap together, said means and said wedges enabling adjustment without disassembly or removal from the patient.

5. An orthopedic foot splint as in claim 1, further comprising a plurality of clutch interfacings for indexing and fixating said splint in adjusted positions, whereby positive and prescribable settings can be achieved.

6. An orthopedic foot splint as in claim 1, further comprising:
   a. a pair of calf cups for affixing said splint to the patient's legs,
   b. a pair of vertical bars for mounting said calf cups,
   c. means for enabling said calf cups and said vertical bars to rotate and tilt with respect to said elongate bar, and
   d. a plurality of adaptors for rotating and tilting said calf cups, and said vertical bars with respect to said elongate bar,
whereby dorsiflexion/plantarflexion, and equinus/equino problems can be corrected.

7. In a modular orthopedic foot splint to which the shoes or feet of a patient are attached, and which comprises:
   a. a pair of top plates to which the shoes or feet of the patient can be attached,
   b. a pair of base plates for mounting the said top plates,
   c. an elongated bar interconnecting said base plates,
   d. means for enabling said top plates to rotate and tilt with respect to said base plates,
   e. means for enabling said base plates to rotate and tilt with respect to said bar,
   f. a plurality of rotating wedges for rotating and tilting said top plates in relation to said base plates, and
   g. a pair of rotating wedges for rotating and tilting said base plates in relation to said bar,
whereby tilting and rotating of said top plates and said base plates can be accomplished with said wedge components, so that the patient's feet can be tilted to protect said patient's subtalar joint, then tilted, and rotated to correct positional deformities.

8. An orthopedic foot splint as in claim 7, further comprising a plurality of flexible bolts, which allow misalignment of the ends of each bolt from the longitudinal axis thereof, said bolts for holding said top plates, said base plates, said rotating wedges, and said bar, in fixed positions relative to each other.

9. The orthopedic foot splint of claim 8 wherein said bolts also comprise a counter-rotational component for preventing rotational torque from being transmitted to a flexible portion thereof, whereby said components can be held in tight proximity one to another and locked in position by said bolts.

10. An orthopedic foot splint as in claim 7, further including means for enabling said foot plates, said wedges, and said bar to snap together, said means and said wedges enabling adjustment without disassembly or removal from the patient.

11. An orthopedic foot splint as in claim 7, further comprising a plurality of clutch interfacings for indexing and fixating said splint in adjusted positions, whereby prescribable and repeatable settings can be achieved.

12. An orthopedic foot splint as in claim 7, further comprising a plurality of top plates whose proximate edges are curved so as to preclude the presentation of sharp edges to the feet of the patient during use.

13. An orthopedic foot splint as in claim 7, further comprising:
   a. a pair of calf cups for affixing said splint to the patient's legs,
   b. a pair of vertical bars for mounting said calf cups,
   c. means for enabling said calf cups and said vertical bars to rotate and tilt with respect to said elongate bar, and
   d. a plurality of adaptors for rotating and tilting said calf cups, and said vertical bars with respect to said elongate bar,
whereby dorsiflexion/plantarflexion, and equinus/equino problems can be corrected.

* * * * *